United States Patent [19]

Murray

[11] Patent Number: 4,668,823

[45] Date of Patent: May 26, 1987

[54] PROCESS FOR THE PREPARATION OF BULKY ALKYLDIARYLPHOSPHINES AND UNSYMMETRICAL ARYLDIALKYL PHOSPHINES

[75] Inventor: Rex E. Murray, Charleston, W. Va.

[73] Assignee: Union Carbide Corporation, Danbury, Conn.

[21] Appl. No.: 567,424

[22] Filed: Dec. 30, 1983

[51] Int. Cl.$^4$ .............................................. C07F 9/50
[52] U.S. Cl. ........................................ 568/17; 549/6; 548/412; 546/21; 568/13
[58] Field of Search ..................... 568/17, 13; 549/6; 548/412; 546/21

[56] References Cited

U.S. PATENT DOCUMENTS

| | | | |
|---|---|---|---|
| 2,912,465 | 11/1959 | Ramsden | 568/17 X |
| 3,099,691 | 7/1963 | Rauhut et al. | 568/17 |
| 3,109,851 | 11/1963 | Ramsden | 568/17 X |
| 3,152,104 | 10/1964 | Rabinowitz et al. | 568/17 X |
| 3,331,878 | 7/1967 | Priestley | 568/17 X |
| 3,499,039 | 3/1970 | Lorenz et al. | 568/17 X |
| 3,723,536 | 3/1973 | Stuebinger et al. | 568/17 |
| 3,751,481 | 8/1973 | Weinberg | 568/17 |
| 3,755,459 | 8/1973 | Diamond | 568/9 |
| 3,804,950 | 4/1974 | Diamond | 424/198 |
| 4,011,267 | 3/1977 | Tamborski et al. | 568/17 |
| 4,036,889 | 7/1977 | Chopdekar et al. | 568/17 |
| 4,045,494 | 8/1977 | Chopdekar et al. | 568/17 X |
| 4,169,861 | 10/1979 | Hughes | 260/604 HF |
| 4,201,728 | 5/1980 | Hughes | 568/454 |
| 4,283,562 | 8/1981 | Billig et al. | 568/454 |

OTHER PUBLICATIONS

Voskuil et al., *Rec. Trav. Chim*, 82: 303–304 (1963).
Voskuil et al., "Organic Synthesis" vol. 5, pp. 221–214 (1973).
Scherer et al., *Chem. Ber.*, 103: 71–75 (1970).
Scherer et al., *Z. Naturforch.* 25b(8): 891–892 (1970).
Ali et al., *J. C. S. Dalton* 638–644 (1980).
K. Sasse, in E. Muller et al., "Methoden der Organischen Chemie (Houben-Weyl)" 4th ed. vol. 12, Part 1, Georg Thieme Verlag, Stuttgart, 1963, pp. 203–205.
Corfield et al., *J. Chem. Soc.* (c) 1930–1933 (1971).
D. Jore et al., *J. Organometal. Chem.* 149: C7–C9 (1978).
Wittig et al., *Leibig's Ann. Chem.* 751: 17–26 (1971).
Burg et al., *Amer. Chem. Soc.* 80: 1107–1109 (1958).
Issleib et al., *Chem. Berichte* 92: 2681 (1959).
Rozanel'skaya et al., *J. Gen. Chem. of the USSR* (English Translation from Zhurnal Obshchei Khimii) 48 (8): 1732–1733 (1978).
Buchner et al., *Amer. Chem. Soc.* 73: 755–756 (1951).
Dmitriev et al., *J. Gen. Chem. of USSR* (English Translation from Zhurnal Obschchei Khimii) 48 (1): 42–44 (1978).
Chodkiewicz et al., *Tetrahedron Letters* No. 12: 1069–1072 (1979).
Dmitriev et al., *J. Gen. Chem. of USSR* (English Translation from Zhurnal Obshchei Khimii) 48 (7): 1405–1408 (1978).
King et al., *J. Org. Chem.* 41 (6): 972–977 (1976).
Chauzov et al., *J. Gen. Chem of USSR* (English Translation from Zhurnal Obshchei Khimii) 43 (1): 66–67 (1973).
Bianco et al., Inorganic Syntheses, vol. XVIII, 169–173 (1978).
Miller, *J. Org. Chem.* 24: 2013–2015 (1959).
Crofts et al., *J. Chem. Soc. (C): 2529–2530 (1970)*.
Crofts et al., *J. Chem. Soc.* (C): 332–336 (1970).
Crofts et al., *J. Chem. Soc.* (C): 2342 (1970).
Davies et al., *J. Chem. Soc.* 276–283 (1944).
Mann et al., *J. Chem. Soc.* 4453–4457 (1952).
Weil, *Helv. Chem. Acta* 37: 654–655 (1954).
Grim et al., *J. Org. Chem.* 32: 781–784 (1967).
S. C. Watson et al., *J. Organometal Chem.* 9: 165–168 (1967).

*Primary Examiner*—Helen M. S. Sneed
*Attorney, Agent, or Firm*—Reynold J. Finnegan

[57] ABSTRACT

A process for the selective production of bulky alkyldiarylphosphines and unsymmetrical dialkylarylphosphines comprising reacting a first Grignard reagent having a bulky alkyl group with an aryldichlorophosphine and thereafter and without isolating the resulting bulky alkylarylchlorophosphine intermediate, reacting said intermediate with a second Grignard reagent having a different, less bullky alkyl group or an aryl group to provide the product phosphine.

9 Claims, No Drawings

PROCESS FOR THE PREPARATION OF BULKY ALKYLDIARYLPHOSPHINES AND UNSYMMETRICAL ARYLDIALKYL PHOSPHINES

BACKGROUND OF THE INVENTION

1. Field of the Invention

This invention relates to a process for the production of bulky alkyldiarylphosphines and unsymmetrical dialkylarylphosphines. More particularly, this invention relates to the use of Grignard reagents to produce these compounds from aryldichlorophosphines.

2. Description of the Prior Art

Aryldialkylphosphines and alkyldiarylphosphines are known to be useful as promoters of rhodium-based catalysts for the hydroformylation of olefins to aldehydes. For example, U.S. Pat. No. 4,283,562 discloses a rhodium-catalyzed hydroformylation process wherein improved catalyst stability is achieved by using as the phosphine ligand a branched-chain alkyldiphenylphosphine, a branched-chain dialkylphenylphosphine, a cycloalkyldiphenylphosphine or a dicycloalkylphenylphosphine.

Alkyldiarylphosphines ($RPAr_2$) and aryldialkylphosphines ($R_2PAr$) may be produced by reacting chlorophosphine precursors, such as chlorodiarylphosphines ($ClPAr_2$) and aryldichlorophosphines ($Cl_2PAr$), with alkylorganometallic compounds (RM), such as a Grignard reagent, as shown in equations (1) and (2):

$$RM + ClPAr_2 \rightarrow RPAr_2 + MCl \quad (1)$$

$$2RM + Cl_2PAr \rightarrow R_2PAr + 2MCl \quad (2)$$

wherein
M=Mg halide, for example
R=alkyl
Ar=Aryl

Unfortunately, since even simple chlorodiarylphosphines are quite expensive, it is difficult to economically produce commercial quantities of the alkyldiarylphosphines from such chlorodiarylphosphines. However, aryldichlorophosphines, such as phenyldichlorophosphine, are available commercially at lower cost than chlorodiarylphosphines. Moreover, aryldichlorophosphines may be manufactured by the Michaelis modification of the Friedel-Crafts reaction as described in *Journal of the American Chemical Society* 73, pp. 755–56 (1951) and as represented by the following equations (3) and (4):

$$ArH + PCl_3 + AlCl_3 \rightarrow ArPCl_2 \cdot AlCl_3 + HCl \quad (3)$$

$$ArPCl_2 \cdot AlCl_3 + OPCl_3 \rightarrow ArPCl_2 + Cl_3AlOPCl_3 \quad (4)$$

wherein Ar=aryl

Scherer and Gick report (*Chem. Ber.* 103, 71–75, 1970) that neither t-butylmagnesium chloride (t-BuMgCl), nor methylmagnesium iodide, when reacted with methyldichlorophosphine ($MePCl_2$) produce pure methyl-t-butylchlorophosphine. However, the same authors subsequently reported a 45% yield of product from the $MePCl_2$/t-BuMgCl route at −20° C. (*Z. Naturforsch.* B 25(8), 891–92, 1970). Similar compounds, ethyl-t-butylchlorophosphine, ethylisopropylchlorophosphine, and isopropyl-t-butylchlorophosphine, have been synthesized from ethyldichlorophosphine, t-butyldichlorophosphine, isopropylmagnesium dichloride and t-butylmagnesium chloride (*J.C.S. Dalton* 638–644, 1980).

It is known that the reaction of one equivalent of phenyl-Grignard reagent, PhMgX, with phenyldichlorophosphine, $PhPCl_2$, does not selectively form chlorodiphenylphosphine, $Ph_2PCl$. In fact, reports on the synthesis of chlorodiarylphosphines from aryldichlorophosphines usually employ organometallic compounds far less reactive than Grignard reagents such as organomercury, organocadmium or organozinc reagents to induce selectivity to chlorodiphenylphosphine formation. (k. Sasse, in E. Muller, "Methoden der Organischen Chemie (Houben-Weyl)" 4th ed., Vol. 12, Part I, Georg Thieme Verlag, Stuttgart, 1963, pp. 203–205). In another reference (*J.C.S.* C 1930–33, 1971), it is reported that t-butyldiphenylphosphine, t-$BuPh_2P$, may be prepared by first producing and isolating chlorophenyl-t-butylphosphine, t-BuPhPCl (by reacting phenyldichlorophosphine, $PhPCl_2$, and t-BuMgCl), and then reacting the t-BuPhPCl with an aryllithium (specifically, phenyllithium, PhLi). These reactions may be represented by the following equations (5) and (6):

$$PhPCl_2 + t\text{-BuMgCl} \rightarrow t\text{-BuPhPCl} + MgCl_2 \quad (5)$$

$$t\text{-BuPhPCl} + PhLi \rightarrow t\text{-BuPh}_2P + LiCl \quad (6)$$

This technique suffers from the disadvantage caused by the additional intermediate isolation step.

D. Jore et al., in *J. Organometal. Chem.* 149, C7–C9 (1978), report that unsymmetrical dialkylphenylphosphines, PhPRR', can be produced from phenyldichlorophosphine, $PhPCl_2$, by first adding an organometallic compound less reactive than Grignard reagents, such as an organocadmium reagent $R_2Cd$ (R=Me or $PhCH_2$), to the $PhPCl_2$ and then adding an organometallic reagent R'M (R'=$PhCH_2$, $CH_3$ or o-$CH_3C_6H_4$; M not being specified), according to the following equations (7) and (8):

$$PhPCl_2 + \tfrac{1}{2}R_2Cd \rightarrow PhP(Cl)R \quad (7)$$

$$PhP(Cl)R + R'M \rightarrow PhPRR' \quad (8)$$

The disadvantage of this method is that the organocadmium reagent is fairly exotic and is expensive to prepare. For example, it is commonly prepared from a methyllithium reagent, MeLi, according to equation (9):

$$2MeLi + CdCl_2 \rightarrow Me_2Cd + 2LiCl \quad (9)$$

The use of $CdCl_2$ and methyllithium (or other organometallic or Grignard reagents) to obtain the organocadmium is economically unattractive for commercial production of phosphines.

A similar approach to triarylphosphines by the sequential additions of two different arylorganometallics to phenyldichlorophosphine was reported by G. Wittig et al. in *Liebig's Ann. Chem.* 851 17–26 (1971). The disclosed process can be described by the following equation (10):

$$ArLi \xrightarrow{ZnCl_2} ArZnCl \xrightarrow{Ar'PCl_2} Ar'P(Cl)Ar \xrightarrow{Ar''Li} Ar'Ar''PAr \quad (10)$$

This method is also not economically attractive for the same reasons.

Another known process to prepare alkylarylchlorophosphines comprises reacting Grignards and phenyldichlorophosphine, purifying the reaction product by distillation, and then adding a second Grignard reagent to prepare tertiary phosphines. A process of this type is disclosed in U.S. Pat. Nos. 3,804,950 and 3,755,459. J. R. Corfield, et al. (*J. Chem. Soc.* C 1930–1933, 1971) have synthesized and isolated t-butylphenylchlorophosphine. The isolated t-butylchlorophenylphosphine is reacted with aryllithium reagents, either phenyllithium or alpha-naphthyllithium to produce t-butyldiphenylphosphine or t-butyl-alpha-naphthylphenyl-phosphine, respectively. The disadvantage of these two methods is the isolation of the alkylarylchlorophosphine intermediates. This approach also makes such methods much less commercially inviting, especially since the alkylarylchlorophosphines are difficult to manipulate due to their extreme air and hydrolytic sensitivities.

Another route to phosphines employs a dialkylamino substituent, $R_2N$, on phosphorus as a blocking group. For example, $R_2NPCl_2$ can be prepared from the reaction of two moles of $R_2NH$ with one mole of $PCl_3$. The P—Cl bonds in $R_2NPCl_2$ are reactive towards Grignards, the N—P bond is not. However, upon treatment with anhydrous hydrogen halides the N—P bond is replaced with a P-halogen bond, which is suitable for Grignard substitution.

U.S. Pat. No. 2,934,564 relates to compounds of the general formula $R_2PX$ wherein R represents an alkyl or aryl group and X represents chlorine, bromine or iodine. For example, the reaction of $Me_2NPCl_2$ (0.42 mole) with p-tolylmagnesium bromide (0.84 mole) produces dimethylamino-di-p-tolylphosphine. The isolated dimethylamino-di-p-tolylphosphine (31.88 mmoles) was treated with 1428 cc (63.75 mmoles) of anhydrous HCl yielding di-p-tolylchlorophosphine, which was purified by distillation. Similarly, Burg, et al. (*J.A.C.S.* 80, 1107–09, 1958) disclose the preparation of chlorodimethylphosphine from $Me_2NPCl_2$ and suggest the viability of a Grignard route to $R_2PR'$-type phosphines. K. Issleib, et al. (*Chem. Berichte* 29, 2682–3008, 1959) have shown that $Et_2NPCl_2$ (Et=ethyl) and cyclohexylmagnesium chloride react in a 1:1.25 molar ratio to form diethylaminocyclohexylchlorophosphine in 57.5% yield. The authors suggest this reaction can be exploited to prepare unsymmetrical chlorophosphines of the type RR'PCl, but no mention is made of the possibility of further reaction to unsymmetrical tertiary phosphines of the type RR'R"P.

All routes using dialkylaminochlorophosphines, $R_2NPCl_2$, are tedious and not commercially attractive since (1) $R_2NPCl_2$ must be generated from $PCl_3$ and $R_2NH$ and subsequently purified, (2) the Grignard is reacted with $R_2NPCl_2$ and the intermediate $R_2NPRCl$ or $R_2NPR_2$ is isolated, (3) $R_2NPRCl$ or $R_2NPR_2$ is converted with HCl to $RPCl_2$ or $R_2PCl$ and then isolated, and (4) $RPCl_2$ or $R_2PCl$ is finally reacted with another Grignard to afford the tertiary phosphines.

Another route to unsymmetrical phosphines $R_2PR'$ through the reaction of $PCl_3$ with mixtures of RMgBr and R'MgBr in stoichiometric proportions of reactants (1:2:1) produces a mixture of tertiary phosphines which cannot be separated into its components either by crystallization or by chromatography (N. A. Rozanel 'Skaya, et al., *Journal of General Chemistry of the USSR-English Translation* 48 (8) 1732–1733, 1978).

The prior art also discloses methods for selectively preparing dichloroalkylphosphines and chlorodialkylphosphines from alkylmagnesium chlorides and phosphorus trichloride. For example, W. Voskuil, et al. [*Rec. Trav. Chim.* 82, 302–304 (1963) and "Organic Syntheses" Vol. 5, pp. 211–214 (1973)] have reported procedures for preparing these compounds. In addition, they list the necessary conditions for obtaining pure chlorophosphines. Subsequently, chlorodineopentylphosphine and dichloroneopentylphosphine have been similarly prepared (R. B. King, et al., *J. Org. Chem.* 41 (6) 972–977, 1976).

SUMMARY OF THE INVENTION

It has now been found that production of bulky alkyldiarylphosphines and unsymmetrical dialkylarylphosphines at high selectivities can be accomplished by the sequential addition of different Grignard reagents to aryldichlorophosphines and without the necessity of isolating intermediate products. In summary, the process of the present invention comprises reacting a first Grignard reagent having a bulky alkyl group with an aryldichlorophosphine followed by reacting the unisolated resulting bulky alkylarylchlorophosphine intermediate product with a second Grignard reagent having a different and less bulky alkyl group or an aryl group to thereby produce selectively bulky alkyldiarylphosphines or unsymmetrical dialkylarylphosphines.

The present invention, which provides a less expensive "one-pot" route to both bulky alkyldiarylphosphines and unsymmetrical dialkylarylphosphines in comparison to prior art processes, is based on the unexpected discovery that the reaction of an aryldichlorophosphine, $ArPCl_2$, with a bulky-alkyl Grignard reagent, RMgX, to form a bulky alkylarylchlorophosphine, ArRPCl, the first step of the process of the present invention, does proceed at temperatures as high as about room temperature (+20° C.) with high selectivity. The high selectivity is remarkable in view of prior literature reports of selective Grignard substitutions to chlorophosphines which typically employ −30° C. to −10° C. reaction temperatures. Since it is known that magnesium halides, MgClX, readily exchange with chlorophosphines, $R_2P(Cl)$, producing halophosphines, $R_2P(X)$, according to equation (11):

$$R_2P(Cl) + MgClX \rightarrow R_2P(X) + MgCl_2 \qquad (11)$$

isolation of the chlorophosphine intermediate becomes particularly troublesome in instances where the Grignard is derived from organic halides other than chlorides. By not isolating the alkylarylchlorophosphine intermediate in the process of the present invention, an additional advantage is derived, namely, the ability of being able to use Grignards derived from any of the organic halides.

DESCRIPTION OF THE PREFERRED EMBODIMENTS

In its broadest aspects, the process of the present invention produces, selectively, unsymmetrical dialkylarylphosphines (RR'PAr) and bulky alkyldiarylphosphines (ArAr'PR) by the sequential addition, to an aryldichlorophosphine (ArPCl₂), of two different Grignard reagents, the first Grignard having a bulky alkyl radical (R) and the second Grignard reagent having a different and a less bulky alkyl radical (R') or an aryl radical (Ar'). The process is performed without isolation and purification of the resulting bulky alkylarylchlorophosphine intermediate (ArP(R)Cl) and thereby offers a pronounced advantage over the prior art processes. The process of the present invention may be represented by the following reaction equations (12)–(14):

$$ArPCl_2 + RMgX \rightarrow ArP(R)Cl \quad (12)$$

$$ArP(R)lCl + Ar'MgX \rightarrow ArAr'PR \quad (13)$$

$$ArP(R)Cl + R'MgX \rightarrow RR'PAr \quad (14)$$

wherein Ar and Ar' each represents an aryl group which may be the same or different, R represents a bulky alkyl group, R' represents an alkyl group different from and less bulky than that represented by R, and X represents a halogen atom. Equation (12) represents the first step of the process of the invention, namely the reaction of an aryldichlorophosphine (ArPCl$_2$) with a bulky-alkyl Grignard reagent (RMgX) to produce a bulky alkylarylchlorophosphine intermediate (ArP(R)Cl). Equations (13) and (14) represent alternate second steps, depending on the product desired. Specifically, equation (13) shows the production of bulky alkyldiarylphosphines (ArAr'PR) by reaction of the unisolated bulky alkylarylchlorophosphine intermediate (ArP(R)Cl) with an aryl Grignard reagent (Ar'MgX), whereas equation (14) shows the production of unsymmetrical dialkylarylphosphines (RR'PAr) by reaction of the unisolated intermediate with a different Grignard, namely an alkyl Grignard reagent (R'MgX) where the alkyl group (R') is different from and less bulky than alkyl group (R).

By "unsymmetrical" dialkylarylphosphines (i.e., RR'PAr) is meant tertiary phosphines having three different substituents: a bulky alkyl group (i.e., R), a different and less bulky alkyl group (i.e., R') and an aryl group (i.e., Ar).

An important aspect of this invention is the order in which the Grignard reagents are added. In order to achieve high selectivities to the bulky alkyldiarylphosphines and unsymmetrical dialkylarylphosphines, it is necessary that the bulky alkyl Grignard (RMgX) be reacted first with the aryldichlorophosphine (ArPCl$_2$), is followed by reacting the resulting intermediate (unisolated) with the second Grignard (Ar'MgX or R'MgX). The high selectivities provided by the present invention are believed to be due to the unexpectedly high selectivities to the bulky alkylarylchlorophosphine intermediates obtained by the first step of the process of the invention. The second step, namely the reaction of the intermediate (ArP(R)Cl) with the second Grignard, is believed to be substantially a quantitative reaction. Therefore, an excess of the second Grignard may be employed in the second step of the process of the invention although it is preferred to use only about an equivalent amount or a slight excess. However, in order to avoid formation of undesired dialkylarylphosphines in the first step, it is preferred that the first Grignard be used in no more than about the equivalent amount.

It is also preferred that in the first step of the process of the invention, the bulky-alkyl Grignard reagent, RMgX, be slowly added to a stirred solvent solution containing the aryldichlorophosphine starting material. Using these conditions, the selective formation of alkylarylchlorophosphines (ArP(R)Cl) is highly favored. It should be noted that in the first step, reaction temperatures higher than $-30°$ C. may be employed with only slight changes in selectivity when the bulky alkyl group of the RMgX Grignard is cyclohexyl. In fact, cyclohexyldiphenylphosphine has been prepared at selectivities of about 94% and 90% with first step reaction temperatures of $+10°$ C. and $+20°$ C., respectively.

Both reactions occurring in the process of the present invention are exothermic and the temperature may be controlled by any suitable means. Generally, the first step of the process of the invention may be conducted in a suitable solvent for the aryldichlorophosphine at a temperature of from about $-70°$ C. to about $+40°$ C., preferably from about $-30°$ C. to about $+20°$ C. High selectivities are achieved at temperatures between about $-10°$ C. and $+10°$ C. The particular temperature employed will depend on many factors, such as the nature and concentration of the reactants, the solvent used, and the effectiveness of agitation during reaction. Lower temperatures generally favor higher selectivities to arylalkylchlorophosphines. The temperature employed in the first step does affect selectivity and may be varied depending upon the results desired and the other reaction conditions encountered. For example, the means employed or available to cool the reaction may have an influence on the particular temperature employed. A higher temperature may offer the advantage of being able to use brine cooling to control reaction temperature and the lower temperatures may require a coolant such as liquid nitrogen.

By the term bulky alkyl, "R" in the first Grignard, RMgX, is meant secondary alkyl, tertiary alkyl, cycloalkyl, and bicycloalkyl groups as well as primary alkyl groups having at least one substituent (e.g., one or more aryl groups or one or more alkyl groups) in the two-position. The bulky alkyl Grignard, RMgX, may be prepared from commercially-available bulky organic halides such as the cyclohexyl, t-butyl, isobutyl and isopropyl halides using known techniques. The order of preference of the bulky alkyls from the standpoint of the yield of arylalkylchlorophosphine intermediates is cyclohexyl>t-butyl>isopropyl>isobutyl. The organic halide precursor can be a chloride, bromide, or iodide although the chloride is usually preferred because of its lower cost.

The most preferred bulky Grignard reagent used in the first step of the process of the invention is cyclohexyl Grignard. However, other bulky alkyl Grignards such as t-butyl and isopropyl have been converted in good yields to t-butyldiphenylphosphine and isopropyldiphenylphosphine, respectively. Based on these results, it is expected that Grignards containing bulky organic radicals having from 3 to about 20 carbon atoms (i.e., secondary alkyl, tertiary alkyl, cycloalkyl and bicycloalkyl groups and primary alkyl groups having at least one substituent in the two-position, and having a total of 3 to about 20 carbon atoms) should be useful in the first step of the process of the invention. Examples of such bulky organic radicals include:
isopropyl
1-phenyl-2-propyl
2-butyl
2-pentyl
3-pentyl
2-hexyl
3-hexyl
2-heptyl
3-heptyl
4-heptyl
2-octyl 3-octyl
4-octyl
2-nonyl
3-nonyl
2-decyl
3-decyl
2-undecyl
3-undecyl
2-hexadecyl
3-hexadecyl
4-hexadecyl
5-hexadecyl
6-hexadecyl
7-hexadecyl
8-hexadecyl
t-Butyl
1,1-dimethyl-2-phenyl ethyl
1,1-dimethylpropyl
1,1,2-trimethylpropyl
1,1-dimethylbutyl
1,1-diethylpropyl
tricyclohexylmethyl
1-adamantyl
cyclopropyl
cyclobutyl
cyclopentyl
1-methylcyclopentyl
2-methylcyclopentyl
3-methylcyclopentyl
cyclohexyl
1-methylcyclohexyl
2-ethylcyclohexyl
3-methylcyclohexyl
3-ethylcyclohexyl
4-methylcyclohexyl
3,3-dimethylcyclohexyl
3,4-dimethylcyclohexyl
3,3,4-trimethylcyclohexyl
3,4,5-trimethylcyclohexyl
4-cyclohexylcyclohexyl
4-phenylcyclohexyl
cycloheptyl
cyclooctyl
cyclononyl
cyclodecyl
cycloundecyl
cyclododecyl
exo-norbornyl
endo-norbornyl
2-bicyclo[2.2.2]octyl
5-norbornen-2-yl
nopinyl
endo 8-tricyclo[5.2.1.0$^{2,6}$]decyl
exo 8-tricyclo[5.2.1.0$^{2,6}$]decyl
2-adamantyl
decahydro-1-napthyl
decahydro-2-napthyl
menthyl
neomenthyl
2-methylpropyl
2-methylbutyl
2,2-diphenylethyl
2,2-dimethylpropyl
2,3-dimethyl butyl
2-ethylhexyl
2-propylheptyl
2-butyloctyl
2-pentylnonyl
2-hexyldecyl
neopentyl A wide variety of aryldichlorophosphines (ArPCl$_2$) may be used in the first step of the process of the invention. These aryldichlorophosphines are commercially available or may be prepared by known techniques, such as the Michaelis Modification of the Friedel-Crafts reaction. The aryldichlorophosphines prepared by this particular method from substituted benzenes are often mixtures of meta and para isomers. Suitable aryldichlorophosphines which are useful in the present invention are compounds with aryl groups having from 4 to about 20 carbon atoms. For purposes of the present invention, the term "aryl" (for both Ar and Ar') is meant to include organic radicals derived from heteroaromatic compounds as well as from aromatic hydrocarbons. Examples of such aryl groups Ar include:

| | |
|---|---|
| phenyl | p-chlorophenyl |
| m-tolyl | 3,4-dichlorophenyl |
| p-tolyl | 3,4,5-trichlorophenyl |
| m-ethylphenyl | 3-bromophenyl |
| p-ethylphenyl | 3,4,5-dibromophenyl |
| m-propylphenyl | 3,4,5-tribromophenyl |
| p-propylphenyl | m-fluorophenyl |
| m-isopropylphenyl | p-fluorophenyl |
| p-isopropylphenyl | p-phenoxyphenyl |
| p-(secondary butyl)phenyl | p-biphenyl |
| m-(tert-butyl)phenyl | m-biphenyl |
| p-(tert-butyl)phenyl | m-acetylphenyl |
| m-(butyl)phenyl | p-acetylphenyl |
| p-(butyl)phenyl | m-trifluoromethylphenyl |
| m-(pentyl)phenyl | p-trifluoromethylphenyl |
| m-(hexyl)phenyl | 2-thienyl |
| p-(hexyl)phenyl | 4-methyl-2-thienyl |
| m-(cyclohexyl)phenyl | 5-methyl-2-thienyl |
| p-(cyclohexyl)phenyl | 3-thienyl |
| m-decylphenyl | 5-methyl-3-thienyl |
| p-decylphenyl | 2-furyl |
| m-dodecylphenyl | 4-methyl-2-furyl |
| p-dodecylphenyl | 5-methyl-2-furyl |
| m-methoxyphenyl | 3-furyl |
| p-methoxyphenyl | 5-methyl-3-furyl |
| 3,4-dimethylphenyl | 2-pyrryl |
| 3,4,5-trimethylphenyl | 1-methyl-3-pyrryl |
| m-chlorophenyl | 4-methyl-2-pyrryl |
| | 3-pyrryl |
| | 2-pyridyl |
| | 3-pyridyl |
| | 4-pyridyl |
| | 1,5-dimethyl-3-pyrryl |

In the second step of the process, an aryl Grignard reagent (Ar'MgX) or an alkyl Grignard reagent (R'MgX) is added to the unisolated alkylarylchlorophosphine intermediate, preferably followed by heating to ensure completion of the reaction. It is also expected that aryl Grignards of the formula Ar'(MgX)$_2$ are useful in the present invention. Strict temperature control of the reaction is not necessary in this step, and an excess of the Grignard reagent may be used without deleterious effects (i.e., without decreasing selectivity to desired products). The second Grignard (Ar'MgX or Ar'(MgX)$_2$ or R'MgX) may be added at any convenient temperature, such as room temperature. Ideally, the second-step reaction can be performed between ambient temperature and the reflux temperature of the solvent. Since the second Grignard reagent completes the tertiary phosphine synthesis it is imperative that sufficient amounts of the second Grignard reagent be present to completely substitute the intermediate phosphine chloride. However, since this reaction proceeds substantially quantitatively, it is preferred that the second Grignard be employed in about an equivalent amount or a slight excess. The second Grignard reagent can be either alkyl or aryl in nature. Suitable alkyl groups R' useful in the second Grignard are those having from 1 to about 20 carbon atoms and suitable aryl groups Ar' (including both aromatic hydrocarbon- and heteroromatic-derived radicals) are those having from 4 to about 20 carbon atoms. Exaples of aryl group Ar' include:

| | |
|---|---|
| phenyl | p-chlorophenyl |
| m-tolyl | 3,4-dichlorophenyl |
| p-tolyl | 3,4,5-trichlorophenyl |
| m-ethylphenyl | 3-bromophenyl |
| p-ethylphenyl | 3,4-dibromophenyl |
| m-propylphenyl | 3,4,5-tribromophenyl |
| p-propylphenyl | m-fluorophenyl |
| m-isopropylphenyl | p-fluorophenyl |
| p-isopropylphenyl | p-phenoxyphenyl |
| p-(secondary butyl)phenyl | p-biphenyl |
| m-(tert-butyl)phenyl | m-biphenyl |
| p-(tert-butyl)phenyl | m-acetylphenyl |
| m-(butyl)phenyl | p-acetylphenyl |
| p-(butyl)phenyl | m-trifluoromethylphenyl |
| m-(pentyl)phenyl | p-trifluoromethylphenyl |
| m-(hexyl)phenyl | 2-thienyl |
| p-(hexyl)phenyl | 4-methyl-2-thienyl |
| m-(cyclohexyl)phenyl | 5 methyl-2-thienyl |
| p-(cyclohexyl)phenyl | 3-thienyl |
| m-decylphenyl | 5-methyl-3-thienyl |
| p-decylphenyl | 2-furyl |
| m-dodecylphenyl | 4-methyl-2-furyl |
| p-dodecylphenyl | 5-methyl-2-furyl |
| m-methoxyphenyl | 3-furyl |
| p-methoxyphenyl | 5-methyl-3-furyl |
| 3,4-dimethylphenyl | 2-pyrryl |
| 3,4,5-trimethylphenyl | 1-methyl-3-pyrryl |
| m-chlorophenyl | 4-methyl-2-pyrryl |
| | 3-pyrryl |
| | 2-pyridyl |
| | 3-pyridyl |
| | 4-pyridyl |
| | 1,5-dimethyl-3-pyrryl |

Examples of alkyl group R' (which may be substituted) include those radicals listed above for R as well as the following additional radicals:

| | |
|---|---|
| methyl | 1-undecyl |
| ethyl | 1-dodecyl |
| 1-propyl | 1-tridecyl |
| 1-butyl | 1-tetradecyl |
| 1-pentyl | 1-pentadecyl |
| 1-hexyl | 1-hexadecyl |
| 1-heptyl | 2-heptadecyl |
| 1-octyl | 1-octadecyl |
| 1-nonyl | benzyl |
| 1-decyl | |

The process of the invention may be performed in any solvent or solvent mixture which is innocuous to both Grignard reagents and the chlorophosphine intermediates. The particular solvent used is not critical. Protic solvents such as alcohols, carboxylic acids and water decompose both phosphorus halides and Grignard reagents and, thus, are not useful. On the other hand, both Grignard reagents and phosphorus halides are stable in anhydrous ethers, tertiary amines, and hydrocarbons as well as in certain mixtures of these solvents. In particular, anhydrous diethyl ether and anhydrous tetrahydrofuran have proven to be useful solvents for this process and are therefore preferred. The same solvent need not be used in each step of the process. Other preferred solvents, commonly used to prepare Grignard reagents, and which can be used in the process of the present invention, include diisopropyl ether, dibutyl ether, and dioxane. Additionally, the glyme ether solvents (including monoglyme, diglyme, triglyme, tetraglyme), tertiary amines, aliphatic hydrocarbons, and aromatic hydrocabons are also useful.

The process of this invention requires intimate mixing of the reactants, especially during Grignard reagent additions. Intimate mixing during the additionof the first Grignard reagent to the aryldichlorophosphine enhances selectivity to the alkylarylchlorophosphine intermediate. Any conventional equipment may be employed in the present invention.

The process should be performed under an atmosphere inert to Grignard reagents and phosphorus halides, both of which are oxygen and moisture sensitive. Thus, "dry", inert gases are preferred such as nitrogen, argon, or helium, as well as others known to those skilled in the art. The total pressure is not critical and generally the process of the invention may be performed at about atmospheric pressure.

After completion of the total reaction sequence, the product phosphine may be isolated from the reaction medium by the use of any known technique, such as those disclosed in U.S. Pat. No. 3,499,039. However, during recovery the resultant aqueous phase should not be strongly acidic, since the phosphine could in that event be extracted into the aqueous phase as the phosphonium salt. In any event, separation of the aqueous and organic layers is desirable. The phosphine may be subsequently isolated by complete distillation of the organic layer or alternatively by concentration of the organic layer and recrystallization of the crude phosphine residue.

The invention will now be further illustrated by way of the following examples and the comparative example, all of which refer to work actually performed. These examples are meant to be illustrative only and are not intended to limit the invention. Rather, it is intended that the invention be limited only by the scope of the claims appended hereto.

EXAMPLE 1

A Grignard mixture of 55 mmoles of cyclohexylmagnesium chloride (prepared from 1.5 g of magnesium turnings and 6.5 g of cyclohexylchloride in 20 ml of anhydrous ether) was added dropwise to a stirred solution of 8.9 g (50 mmoles) of phenyldichlorophosphine in 50 ml of anhydrous ether maintained under an inert atmosphere at −25° C. After the addition was complete, the resulting mixture was allowed to gradually warm to ambient temperature and then was refluxed for 15 minutes. The stirred mixture was cooled and a solution of 75 mmoles of isopropylmagnesium bromide (prepared from 2.1 g of magnesium turnings and 9.5 g of isopropyl bromide in 29 ml of anhydrous ether) was added dropwise at temperatures between 0° C. and +30° C. After refluxing for 4 hours, the reaction mixture was cooled to 0° C. and treated dropwise with 25 ml of water, thereby giving two phases. The ether phase was separated, dried over magnesium sulfate, concentrated, and distilled to give cyclohexylisopropylphenylphosphine: $^{31}$P-NMR $\delta = 6.08$ ppm; boiling point ("BP")=104°-105° C. at 0.05 torr, Chemical Ionization Mass Spec [M+H$^+$=235, yield=about 67%.

EXAMPLE 2

211 ml of a 1.72 Molar titrated solution of 0.36 mole of cyclohexylmagnesium chloride in diethyl ether was added dropwise to a stirred solution of 75 g (0.36 mole) of isomeric m- and p-ethylphenyldichlorophosphine in 400 ml of anhydrous ether maintained at −30° C. under an inert atmosphere. After stirring at −30° C. for 15 minutes the solution was allowed to gradually warm to 0° C. A mixture of 0.54 mole of phenylmagnesium bromide (prepared from 14.5 g. of magnesium turnings and 85.3 g of bromobenzene in 330 ml of anhydrous ether) was added dropwise to the warmed solution at a temperature of between 0° C. and +7° C. The reaction mixture was then heated to reflux for 30 minutes, cooled to +15° C., and 150 ml of water was slowly added. After acidifying the aqueous layer by the addition of 21 ml of concentrated hydrochloric acid to dissolve the magnesium salts, 15 ml of concentrated ammonium hydroxide was added to adjust the pH of the aqueous layer to between 8 and 9. The ether layer was separated, dried over magnesium sulfate, and concentrated to form a yellow oil. Distillation of the residue gave an isomeric mixture of cyclohexyl (m- and p-ethylphenyl)-phenylphosphine which crystallized upon standing: Yield=about 90%, B.P.=173°-175° C. at 0.15 torr, $^{31}$P-NMR $\delta$=−3.99 ppm (relative intensity 719.53) and $\delta$=5.19 ppm (relative intensity 999.96).

EXAMPLE 3

When isomeric meta- and para-isopropylphenyldichlorophosphine (80 g, 0.36 mole) was substituted for meta- and para-ethylphenyldichlorophosphine in Example 2, meta- and para-isopropylphenylcyclohexylphenylphosphine was obtained. $^{31}$P-NMR $\delta$=−4.04 ppm (relative intensity 41.90) and $\delta$=−5.555 ppm (relative intensity 99.99) Yield=about 78%, BP=190°-193° C. at 0.15 torr.

COMPARATIVE EXAMPLE 1

A 2.17 Molar solution of 180 mmoles of t-butyllithium in 65 ml of pentane was added dropwise to 65 ml of a stirred solution of 45.0 g (179 mmoles) of isomeric m- and p-biphenyldichlorophosphine in 400 ml of anhydrous ether maintained at −50° C. under an inert atmosphere. After the addition was complete the mixture was stirred for 15 minutes at −50° C. and then allowed to gradually warm to +20° C. A 2.0 Molar solution of 212 mmoles of phenylmagnesium bromide in 106 ml of ether was added dropwise while the temperature was maintained between +20° C. and +27° C. The mixture was refluxed for one-half hour and cooled to +10° C. Water (60 ml) and then concentrated hydrochloric acid (5 ml) were successively added, dropwise. The aqueous phase was made alkaline (to pH=8-9) with concentrated ammonium hydroxide. The ether phase was separated, dried with magnesium sulfate, and concentrated to a yellow oil. Distillation gave a yellow solid containing biphenyl(t-butyl)phenylphosphines.

$^{31}$P-NMR $\delta$=−4.47 ppm (relative intensity 471.48)
$\delta$=−4.74 ppm (relative intensity 251.55)
$\delta$=−5.88 ppm (relative intensity 999.96)
Yield about 16%
BP=143°-173° C. at 0.10 torr.

EXAMPLE 4

49 ml of a 1.72 Molar titrated solution of 84 mmoles of cyclohexylmagnesium chloride in ether was added dropwise to a stirred solution of 19.8 g (84.1 mmoles) of m- and p-t-butylphenyldichlorophosphine in 100 ml of anhydrous ether, maintained at 0° C. under an inert atmosphere. After the addition was complete, the solution was stirred for 15 minutes at 0° C., then a 2.0 Molar solution of 126 mmoles of phenylmagnesium bromide in 63 ml of ether was added dropwise at a temperature of between 0° and +13° C. After warming to reflux for one-half hour, hydrolysis was performed. Distillation of the concentrated residue gave a produce with a $^{31}$P-NMR $\delta$=−4.59 ppm (relative intensity 499.98) and $\delta$=−6.37 ppm (relative intensity 115.66), Yield=about 58%. BP=164°-158° C. at 0.15 torr.

EXAMPLE 5

85 ml of a 1.72 Molar titrated solution of 147 mmoles of cyclohexylmagnesium chloride in ether was added dropwise to a stirred solution of 34.4 g (147 mmoles) of m- and p-sec-butyldichlorophosphine in 200 ml of anhydrous ether, maintained at −10° C. under an inert atmosphere. The solution was then stirred for 15 minutes at −10° C. and then allowed to warm to 0° C. A 2.0 Molar solution of 220 mmoles of phenylmagnesium bromide in 110 ml of ether was then added dropwise as the temperature was maintained at between 0° and +17° C. After warming to reflux for one-half hour and hydrolysis, distillation of the concentrated residue gave (m- and p-sec-butylphenyl)cyclohexylphenylphosphine. $^{31}$P-NMR $\delta$=−3.68 ppm (relative intensity 256.79) and $\delta$=−5.09 ppm (relative intensity 499.96), Yield=about 78%. BP=190°-193° C. at 0.15 torr.

EXAMPLE 6

Using the procedure of Example 4, but replacing the 84 mmoles of (p-t-butylphenyl)dichlorophosphine with 104 mmoles of (p-cyclohexylphenyl)-dichlorophosphine and using, correspondingly, 104 mmoles of cyclohexylmagnesium chloride, a solid residue was provided. A recrystallization of the residue from ethanol gave (p-cyclohexylphenyl)-cyclohexylphenylphosphine. $^{31}$P-NMR $\delta$=−4.47 ppm (relative intensity 999.43). Yield=about 41%, Melting Point (MP)=124°-126.5° C.

EXAMPLE 7

154 ml of a 1.72 Molar titrated solution of 0.266 mole of cyclohexylmagnesium chloride in ether was added dropwise to a stirred solution of 47.54 g (0.2656 mole) of phenyldichlorophosphine in 400 ml of anhydrous ether, maintained at +10° C. under an inert atmosphere. After the addition was complete the mixture was stirred for 15 minutes at +10° C. A 2.0 Molar solution of 0.319 mole of phenylmagnesium bromide in 159 ml of ether was then added dropwise at a temperature of between +10° and +22° C. The mixture was warmed to reflux for one-half hour, then cooled to +6° C. and treated dropwise with 160 ml of water then 14 ml of concentrated hydrochloric acid. The mixture was made basic with 10 ml of concentrated ammonium hydroxide (to pH=9) and the ether phase was separated, dried with magnesium sulfate and concentrated to yield a yellow waxy solid. Recrystallization from ethanol gave cyclohexyldiphenylphosphine. MP=52.5°-57.5° C., $^{31}$P-NMR $\delta$=−1.97 ppm (relative intensity 999.93) and $\delta$=−1.25 ppm (dicyclohexylphenylphosphine impurity-relative intensity=13.25), Yield=about 70%.

EXAMPLE 8

466 ml of a 1.06 Molar titrated solution of 494 mmoles of t-butylmagnesium chloride in 466 ml of ether was added dropwise to a stirred solution of 88.4 g (494 mmoles) of phenyldichlorophosphine in 750 ml of anhydrous ether, maintained at +10° C. under an inert atmosphere. After the addition was complete the mixture was stirred for 15 minutes at +10° C., then the reaction mixture was allowed to gradually warm to ambient temperature. A Grignard mixture of 741 mmoles of phenylmagnesium bromide (prepared from 116.4 g of bromobenzene and 19.8 g of magnesium turnings in 450 ml of anhydrous ether) was added dropwise at +27° C., and the reaction mixture was then refluxed for 18 hours. The mixture was cooled to +18° C., and 340 ml of water was added dropwise at a temperature of between +18° C. and +36° C. After treatment with concentrated hydrochloric acid and ammonium hydroxide distillation gives t-butyldiphenylphosphine. $^{31}$P-NMR(delta)=17.53 ppm (relative intensity 1000.59), Yield=about 46%, BP=120°-125° C. at 0.2 torr.

EXAMPLE 9

193 ml of a 2.6 Molar solution of 503 mmoles of isopropylmagnesium bromide in ether was added dropwise to a stirred solution of 89.96 g (502.6 mmoles) of phenyldichlorophosphine in 750 ml of anhydrous ether, maintained at −25° C. under an inert atmosphere. After the addition was complete, the mixture was stirred for 15 minutes at a temperature of −25° C. and then was allowed to gradually warm to +8° C. 325 ml of a 2.01 Molar solution of 653 mmoles of phenylmagnesium bromide in ether was then added dropwise at a temperature of between +8° C. to +32° C. The mixture was refluxed for one-half hour, and hydrolyzed. Distillation gave isopropyldiphenylphosphine. $^{31}$P-NMR(delta)=0.49 ppm (relative intensity 999.96), Yield=about 49%, BP=122°-124° C. at 0.3 torr.

EXAMPLE 10

265 ml of a 1.8 Molar titrated solution of 477 mmoles of isobutylmagnesium iodide in ether was added dropwise to a stirred solution of 85.35 g (476.8 mmoles) of phenyldichlorophosphine in 750 ml of anhydrous ether, maintained at −25° C. under an inert atmosphere. After stirring for 15 minutes at a temperature of −25° C., the reaction mixture was allowed to gradually warm to a temperature of 0° C. 308 ml of a 2.01 Molar solution of 620 mmoles of phenylmagnesium bromide in ether was added dropwise at a temperature of between 0° C. and +10° C., then the solution was warmed to reflux for one-half hour. The mixture was then hydrolyzed. Distillation yielded an impure isobutyldiphenylphosphine. $^{31}$P-NMR $\delta$=−20.66 ppm (relative intensity 999.96), $\delta$=−5.88 ppm (relative intensity 26.64 probably triphenylphosphine), $\delta$=−34.23 ppm (relative intensity 74.75, probably diisobutylphenylphosphine), and $\delta$=−60.57 ppm (relative intensity 123.65, probably (phenyl)(i-butyl)PH), BP=97°-101° C. at 0.15 torr.

EXAMPLE 11

To a stirred solution of 10 mmoles of phenyldichlorophosphine in 19.7 ml of anhydrous ether, maintained at −25° under an inert atmosphere, was added dropwise 4.0 ml of a 2.48 Molar solution of 10 mmoles of n-heptylmagnesium chloride in ether. After stirring for 15 minutes at −25° C., the reaction mixture was allowed to warm to +17° C. 6 ml of a 2.01 Molar solution of 12 mmoles of phenylmagnesium bromide in ether was added dropwise and then the reaction mixture was refluxed for one-half hour. After cooling to ambient temperature and diluting with 10 ml of hexane, the supernatant solution was analyzed. $^{31}$P-NMR $\delta$=−5.34 ppm (relative intensity 21.64, triphenylphosphine), $\delta$=−16.6 ppm (relative intensity 40.80, di-n-heptylphenylphosphine), and $\delta$=−25.9 ppm (relative intensity 99.99, n-heptyldiphenylphosphine).

EXAMPLE 12-17

These examples show the importance of the sequence in which the Grignard reagents are added and the effect of the temperature at which the first Grignard reagent is added. Example 12 was conducted as follows: To 19.7 ml of a stirred solution of 10 mmoles of phenyldichlorophosphine in anhydrous ether maintained at −10° C. under an inert atmosphere, was added dropwise 5.8 ml of a titrated 1.72 Molar solution of 10 mmoles of cyclohexylmagnesium chloride. After stirring for 15 minutes at −10° C. the reaction mixture was allowed to gradually warm to +18° C. 6 ml of a 2.0 Molar solution of 12 mmoles of phenylmagnesium bromide in ether was added dropwise at a temperature between +18° C. and +31° C., and then the reaction mixture was heated to reflux for 20 minutes. The mixture was cooled to ambient temperature diluted with 10 ml of hexane, stirred about 1 hour, and the salts were allowed to settle. A sample of the organic phase was submitted for $^{31}$P-NMR analysis.

Examples 13–17 were conducted under the same conditions as Example 12, with the following exceptions: In Example 13, the cyclohexylmagnesium chloride was added at a temperature of +10° C. In Examples 14 and 15, the temperatures of addition of the first Grignard (cyclohexylmagnesium chloride) were +20° C. and the +33° C., respectively. In Example 16 the Grignards were reversed and phenylmagnesium bromide (10 mmoles) was added in the first step and cyclohexylmagnesium chloride was added in the second step. In Example 17, the Grignards were reversed and phenylmagnesium bromide (10 mmoles) was added at a temperature of +10° C. in the first step, and cyclohexylmagnesium chloride (12 mmoles) was added in the second step. The results are shown in the following table.

| Example | Order of Grignard Addition | Temperature of First Grignard Addition (°C.) | Product Selectivity (%)[a] |
|---|---|---|---|
| 12 | Cyclohexyl/Phenyl | −10 | 95 |
| 13 | Cyclohexyl/Phenyl | +10 | 94 |
| 14 | Cyclohexyl/Phenyl | +20 | 90 |
| 15 | Cyclohexyl/Phenyl | +33 | 76 |
| 16 | Phenyl/Cyclohexyl | −10 | 27 |
| 17 | Phenyl/Cyclohexyl | +10 | 25 |

[a]Selectivity of cyclohexyldiphenylphosphine, determined by comparing the reaction mixture spectra with the spectra of synthetic standards containing cyclohexyldiphenylphosphine, triphenylphosphine and dicyclohexylphenylphosphine.

The results of these examples clearly show that the bulky (i.e., cyclohexyl) Grignard must be added first in the reaction sequence to achieve high selectivity to cyclohexyldiphenylphosphine. When the cyclohexyl Grignard reagent was added first, its temperature of addition had little influence on the selectivity except that at +33° C., the selectivity dropped from 90% or more to 76%, still significantly higher than that achieved when the order of Grignard addition was reversed.

What is claimed is:

1. A process for selectively producing a product phosphine selected from the class consisting of bulky alkyldiarylphosphine of the formula ArAr'PR or unsymmetrical dialkylarylphosphines of the formula R'RP Ar, wherein R represents a bulky alkyl group having from 3 to 20 carbon atoms selected from the group consisting of secondary alkyls, tertiary alkyls, cycloalkyls, bicycloalkyls, and primary alkyls having at least one substituent in the two-position, wherein R' represents a different alkyl group having from 1 to 20 carbon atoms and being less bulky than said R, and wherein Ar and Ar' each represent the same or different aryl group, each having from 4 to 20 carbon atoms, comprising (1) slowly adding about an equimolar amount of a first Grignard reagent of the formula RMgX, where X represents a halogen atom and R is the same as defined above, at a temperature of about $-70°$ C. to about $+40°$ C., to an aryldichlorophosphine of the formula $ArPCl_2$, where Ar is the same as defined above, and reacting same, to produce a bulky alkylarylchlorophosphine intermediate of the formula ArP(R)Cl, where Ar and R are the same as defined above, and (2) without isolating said intermediate thereafter slowly adding at least about an equimolar amount of a second Grignard reagent of the formula R'MgX, Ar'MgX or Ar'(MgX)$_2$, where Ar', X and R' are the same as defined above to said intermediate and reacting same, to thereby produce the product phosphine.

2. The process of claim 1 wherein the bulky alkyl group R is selected from the group consisting of
isopropyl
1-phenyl-2-propyl
2-butyl
2-pentyl
3-pentyl
2-hexyl
3-hexyl
2-heptyl
3-heptyl
4-heptyl
2-octyl
3-octyl
4-octyl
2-nonyl
3-nonyl
2-decyl
3-decyl
2-undecyl
3-undecyl
2-hexadecyl
3-hexadecyl
4-hexadecyl
5-hexadecyl
6-hexadecyl
7-hexadecyl
8-hexadecyl
t-Butyl
1,1-dimethyl-2-phenyl ethyl
1,1-dimethylpropyl
1,1,2-trimethylpropyl
1,1-dimethylbutyl
1,1-diethylpropyl
tricyclohexylmethyl
1-adamantyl
cyclopropyl
cyclobutyl
cyclopentyl
1-methylcyclopentyl
2-methylcyclopentyl
3-methylcyclopentyl
cyclohexyl
1-methylcyclohexyl
2-methylcyclohexyl
2-ethylcyclohexyl
3-methylcyclohexyl
3-ethylcyclohexyl
4-methylcyclohexyl
3,3-dimethylcyclohexyl
3,4-dimethylcyclohexyl
3,3,4-trimethylcyclohexyl
3,4,5-trimethylcyclohexyl
4-cyclohexylcyclohexyl
4-phenylcyclohexyl
cycloheptyl
cyclooctyl
cyclononyl
cyclodecyl
cycloundecyl
cyclododecyl
exo-norbornyl
endo-norbornyl
2-bicyclo[2.2.2]octyl
5-norbornen-2-yl
nopinyl
endo 8-tricyclo[5.2.1.0$^{2,6}$]decyl
exo 8-tricyclo[5.2.1.0$^{2,6}$]decyl
2-adamantyl
decahydro-1-napthyl
decahydro-2-napthyl
menthyl
neomenthyl
2-methylpropyl
2-methylbutyl
2,2-diphenylethyl
2,2-dimethylpropyl
2,3-dimethyl butyl
2-ethylhexyl
2-propylheptyl
2-butyloctyl
2-pentylnonyl
2-hexyldecyl and
neopentyl.

3. The process of claim 1 wherein said aryl groups Ar and Ar' are selected from the group consisting of

| | |
|---|---|
| phenyl | p-chlorophenyl |
| m-tolyl | 3,4-dichlorophenyl |
| p-tolyl | 3,4,5-trichlorophenyl |
| m-ethylphenyl | 3-bromophenyl |
| p-ethylphenyl | 3,4,5-dibromophenyl |
| m-propylphenyl | 3,4,5-tribromophenyl |
| p-propylphenyl | m-fluorophenyl |
| m-isopropylphenyl | p-fluorophenyl |
| p-isopropylphenyl | p-phenoxyphenyl |
| p-(secondary butyl)phenyl | p-biphenyl |
| m-(tert-butyl)phenyl | m-biphenyl |
| p-(tert-butyl)phenyl | m-acetylphenyl |
| m-(butyl)phenyl | p-acetylphenyl |
| p-(butyl)phenyl | m-trifluoromethylphenyl |
| m-(pentyl)phenyl | p-trifluoromethylphenyl |
| m-(hexyl)phenyl | 2-thienyl |
| p-(hexyl)phenyl | 4-methyl-2-thienyl |
| m-(cyclohexyl)phenyl | 5-methyl-2-thienyl |
| p-(cyclohexyl)phenyl | 3-thienyl |
| m-decylphenyl | 5-methyl-3-thienyl |
| p-decylphenyl | 2-furyl |

| -continued | |
|---|---|
| m-dodecylphenyl | 4-methyl-2-furyl |
| p-dodecylphenyl | 5-methyl-2-furyl |
| m-methoxyphenyl | 3-furyl |
| p-methoxyphenyl | 5-methyl-3-furyl |
| 3,4-dimethylphenyl | 2-pyrryl |
| 3,4,5-trimethylphenyl | 1-methyl-3-pyrryl |
| m-chlorophenyl | 4-methyl-2-pyrryl |
| | 3-pyrryl |
| | 2-pyridyl |
| | 3-pyridyl |
| | 4-pyridyl and |
| | 1,5-dimethyl-3-pyrryl. |

4. The process of claim 2 wherein said alkyl group R' is selected from the group consisting of those radicals listed in claim 2 and

| | |
|---|---|
| methyl | 1-undecyl |
| ethyl | 1-dodecyl |
| 1-propyl | 1-tridecyl |
| 1-butyl | 1-tetradecyl |
| 1-pentyl | 1-tetradecyl |
| 1-hexyl | 1-pentadecyl |
| 1-heptyl | 1-hexadecyl |
| 1-octyl | 2-heptadecyl |
| 1-nonyl | 1-octadecyl and |
| 1-decyl | benzyl. |

5. The process of claim 1 wherein the reaction between said first Grignard and said aryldichlorophosphine is conducted at a temperature between about −30° C. to about +20° C.

6. The process of claim 1 wherein the reaction between said intermediate and said second Grignard is conducted at about room temperature.

7. The process of claim 1 wherein said bulky alkyl group R is cyclohexyl, t-butyl, isopropyl or isobutyl.

8. The process of claim 7 wherein both of said aryl groups Ar and Ar' are phenyl groups.

9. The process as defined in claim 1, wherein said bulky alkyl group is cyclohexyl and wherein both of said aryl groups Ar and Ar' are phenyl groups.

* * * * *